United States Patent
Nguyen

(10) Patent No.: US 8,841,609 B2
(45) Date of Patent: Sep. 23, 2014

(54) DETECTION APPARATUS AND METHODS UTILIZING ION MOBILITY SPECTROMETRY

(71) Applicant: Autoclear LLC, Fairfield, NJ (US)

(72) Inventor: Dao Hinh Nguyen, Ottawa (CA)

(73) Assignee: Autoclear LLC, Garfield, NJ (US)

( * ) Notice: Subject to any disclaimer, the term of this patent is extended or adjusted under 35 U.S.C. 154(b) by 0 days.

(21) Appl. No.: 14/062,595

(22) Filed: Oct. 24, 2013

(65) Prior Publication Data

US 2014/0117222 A1  May 1, 2014

Related U.S. Application Data

(60) Provisional application No. 61/719,185, filed on Oct. 26, 2012.

(51) Int. Cl.
| | |
|---|---|
| *H01J 49/00* | (2006.01) |
| *G01N 27/64* | (2006.01) |
| *G01N 27/62* | (2006.01) |
| *H01J 47/00* | (2006.01) |

(52) U.S. Cl.
CPC .......... *G01N 27/622* (2013.01); *H01J 49/0009* (2013.01); *H01J 47/005* (2013.01); *H01J 49/00* (2013.01)
USPC ........................... 250/282; 250/281; 250/288

(58) Field of Classification Search
CPC .. G01N 27/622; H01J 47/005; H01J 49/0009; H01J 49/00
USPC .................................................. 250/281–300
See application file for complete search history.

(56) References Cited

U.S. PATENT DOCUMENTS

| | | | | |
|---|---|---|---|---|
| 5,294,794 A * | 3/1994 | Davies | ............... | 250/287 |
| 5,552,600 A * | 9/1996 | Davies et al. | ............... | 250/286 |
| 5,796,099 A * | 8/1998 | Jackson | ............... | 250/286 |
| 7,081,618 B2 | 7/2006 | Laprade | | |
| 7,154,086 B2 | 12/2006 | Laprade | | |
| 7,705,296 B2 * | 4/2010 | Wu | ............... | 250/282 |
| 8,084,732 B2 | 12/2011 | Laprade | | |
| 2009/0032699 A1 * | 2/2009 | Morley et al. | ............... | 250/282 |
| 2009/0206839 A1 * | 8/2009 | Seeber et al. | ............... | 324/320 |
| 2012/0003748 A1 * | 1/2012 | Robinson et al. | ............... | 436/173 |

OTHER PUBLICATIONS

Armenta S.; Alcala M.; Blanco M. Analytica Chimica Acta 703 (2011) 114-123.

(Continued)

*Primary Examiner* — Michael Logie
(74) *Attorney, Agent, or Firm* — Lowenstein Sandler LLP

(57) ABSTRACT

A method of and system for analyzing ion mobility of a sample. The sample is received by an ionization chamber, which ionizes molecules of the sample. The ionized sample is received from the ionization chamber by a drift tube coupled to the ionization chamber and propelled along a length of the drift tube in a first direction away from the ionization chamber by an electric field gradient of the drift tube. A magnitude of the electric field gradient is in view of an atmospheric pressure measurement. A drift gas is propelled through the drift tube in a second direction opposite the first direction such that different types of ionized molecules travel through the drift tube at different rates. An arrival time of each of the different types of molecules at a detector located at a second end of the drift tube opposite the first end is detected.

19 Claims, 16 Drawing Sheets

(56) References Cited

OTHER PUBLICATIONS

Eiceman, G.A., Karpas, Z., Ion Mobility Spectrometry. Second Edition. 2005, CRC Press, Boca Raton, FL.

M. Kwasnik et. al.; "Performance, Resolving Power, and Radial Ion Distributions of a Prototype Nanoelectrospray Ionization Resistive Glass Atmospheric Pressure Ion Mobility Spectrometer", Anal. Chem. 2007, 79, 7782-7791.

M. Kwasnik and F.M. Fernandez; "Theoretical and experimental study of the achievable separation power in resistive-glass atmospheric pressure Ion mobility spectrometery", Rapid Commun. Mass Spectrom. 2010, 24, 1911-1918.

Hill, H. H. et. al.; "Resistive Glass IM-TOMS", Anal. Chem. 2010, 82, 9336-9343.

* cited by examiner

DETECTION APPARATUS AND METHODS UTILIZING ION MOBILITY SPECTROMETRY

PRIORITY CLAIM

This application claims the benefit of U.S. Provisional Application Ser. No. 61/719,185 filed on Oct. 26, 2012, which is hereby incorporated by reference.

TECHNICAL FIELD

Embodiments of the invention relate generally to ion mobility spectrometry and, more specifically, to an apparatus and methods using ion mobility spectrometry for the detection of substances.

BACKGROUND

Ion mobility spectrometry (IMS) is an analytical technique that is commonly used for the detection of volatile and semi-volatile substances based on the mobility (drift time or reduced mobility) of ionized molecules of the substance in a gas inside an electric field. IMS can be suitable for applications including detection of illicit substances such as traces of explosives, narcotics or chemical warfare agents.

In a detection instrument using IMS, a drift region of a drift tube is an area between an ion shutter (or gate) and a detector. A conventional stacked drift tube is composed of a series of alternating conductive and insulating rings (e.g., where thickness varies with different designs) stacked together to form a tube of any desirable length. In the drift region, different ion species are subjected to a weak electrical field, causing them to move toward a detector. A drift gas is introduced into the drift region and made to flow opposite to the direction of ion travel. Ion species, thus, continuously collide with the counter flow drift gas, which causes them to slow down relative to each other depending on their collision cross-sectional area. As a result, different ions travel at different rates through the drift region. Longer drift regions provide more time for ions of different species to separate, which increases resolution and lowers signal intensity.

Performance features, such as resolution, signal-to-noise ratio, and durability, are greatly affected by the materials used in the construction of the drift tube, and the linearity of the electric field applied to propel the ions toward the detector. However, IMS instruments should be serviceable and easily maintained.

Gas-ion chemistry under ambient pressure can be complicated in an uncontrolled environment. Temperature, moisture, pressure, electric field, gas flow rates, drift gas composition, and ion density are factors in governing an ion's identity, drift time, peak intensity, and resolving power. Optimizing these parameters can be useful for the detection of compounds of interest.

SUMMARY OF THE INVENTION

An embodiment of the present invention is directed to an apparatus for analyzing a sample. The apparatus includes an ionization chamber that receives the sample and ionizes molecules of the sample, and a drift tube coupled to the ionization chamber at a first end of the drift tube that receives the sample from the ionization chamber. The drift tube has an electric field gradient along its length that propels the sample in a first direction away from the ionization chamber, wherein a magnitude of the electric field gradient is in view of an atmospheric pressure measurement. The apparatus also includes a drift gas supply coupled to the drift tube that propels a drift gas through the drift tube in a second direction opposite the first direction such that different types of ionized molecules travel through the drift tube at different rates. Additionally, a detector at a second end of the drift tube opposite the first end detects an arrival time of each of the different types of ionized molecules.

The apparatus may also include a suction device coupled to the ionization chamber that draws the sample into the ionization chamber. The apparatus can include a gate between the ionization chamber and the drift tube to maintain the sample in the ionization chamber until the gate is opened when a measurement cycle is initiated. The ionization chamber and the gate can have a substantially similar electrical potential until the electrical potential of the ionization chamber is pulsed to a higher electrical potential when the measurement cycle is initiated to propel the sample into the drift tube.

The apparatus can also include a heated port coupled to the ionization chamber, where the heated port receives sample particulate on a sampling screen and desorbs the sample particulate from the sampling screen into the ionization chamber. The drift tube can be formed of glass.

The detector can be a Faraday plate collector. The apparatus can also include a focusing ring located between the drift tube and the detector that directs ionized molecules from the sample towards the detector. The detector can be a pin collector, and the focusing ring can direct the ionized molecules towards the pin collector.

An embodiment of the present invention is directed to an apparatus for analyzing a sample. The apparatus includes an ionization chamber that receives the sample and ionizes molecules of the sample by exposure to a radioactive source having radioactivity in a range from about 100 microcurie to about 1000 microcurie, and a drift tube coupled to the ionization chamber at a first end of the drift tube that receives the sample from the ionization chamber. The drift tube has an electric field gradient along its length that propels the sample in a first direction away from the ionization chamber. The apparatus also includes a drift gas supply coupled to the drift tube that propels a drift gas through the drift tube in a second direction opposite the first direction such that different types of ionized molecules travel through the drift tube at different rates. Additionally, a detector at a second end of the drift tube opposite the first end detects an arrival time of each of the different types of ionized molecules.

An embodiment of the present invention is directed to a method of analyzing a sample. The method includes receiving the sample and ionizing molecules of the sample by an ionization chamber, and receiving the sample from the ionization chamber by a drift tube coupled at a first end to the ionization chamber. The method also includes propelling the sample along a length of the drift tube in a first direction away from the ionization chamber by an electric field gradient of the drift tube and propelling a drift gas from a drift gas supply coupled to the drift tube through the drift tube in a second direction opposite the first direction such that different types of ionized molecules travel through the drift tube at different rates. A magnitude of the electric field gradient is in view of an atmospheric pressure measurement. Additionally, the method includes detecting an arrival time of each of the different types of ionized molecules at a detector located at a second end of the drift tube opposite the first end.

BRIEF DESCRIPTION OF THE DRAWINGS

The present invention is illustrated by way of example, and not by way of limitation, and will become apparent upon consideration of the following detailed description, taken in conjunction with the accompanying drawings, in which like reference characters refer to like parts throughout, and in which.

DETAILED DESCRIPTION

Figure 1:
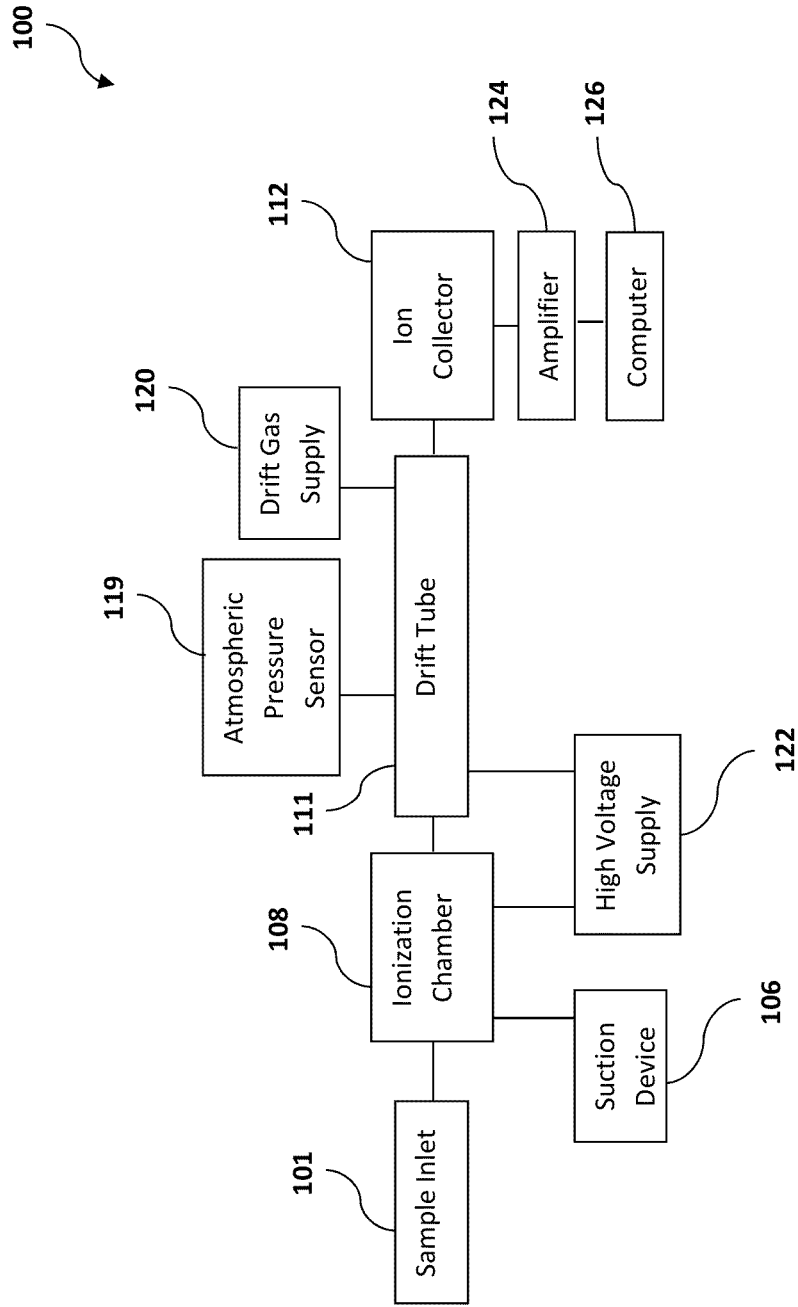
FIG. 1 is a block diagram illustrating an exemplary interconnection of elements of a detection instrument using IMS in accordance with an embodiment of the present invention.

In the following description, numerous details are set forth. It will be apparent, however, to one skilled in the art, that the present invention may be practiced without these specific details. In some instances, well-known structures and devices are shown in block diagram form, rather than in detail, in order to avoid obscuring the present invention.

Embodiments of the present invention provide a method of and system for analyzing ion mobility of a sample, such as particles or vapor that could indicate the presence of narcotics, chemical weapons, explosives, or other illicit substances. In one embodiment, the sample is received and molecules of the sample are ionized by an ionization chamber. The sample is then received from the ionization chamber by a drift tube coupled to the ionization chamber and propelled along a length of the drift tube away from the ionization chamber by an electric field gradient. The electric field gradient may be adjusted based on an atmospheric pressure measurement. A drift gas is propelled through the drift tube opposite the direction that the sample is being propelled such that different types of ionized molecules travel through the drift tube at different rates. For example, different types of molecules can travel at different rates through the drift tube due to different collision cross-sectional areas. An arrival time of each of the different types of ionized molecules at a detector located at an end of the drift tube opposite the ionization chamber is detected. Based on the arrival times of the different types of molecules at the detector, the sample can be analyzed to determine the types of molecules that may present in the sample to determine the types of substances in the sample, such as whether the sample includes narcotics, chemical weapons, or explosives In one embodiment, the apparatus is an instrument, such as a portable instrument or desktop-type instrument, that includes a sample collector to trap vapor or particulate samples, and a desorber to thermally vaporize the chemicals in the sample. A pump can be provided to direct the vapors from the desorber into a reaction zone (e.g., an ionization chamber), which contains an ionization source (e.g., a source with a low level of radioactivity) to ionize molecules in the sample. A gate (e.g., an ion shutter grid) can be placed adjacent to the reaction zone to maintain the ionized molecules in that region between analysis (or measurement) cycles. In one embodiment, a continuous ionization source is used, and the gate maintains the ionized sample in the ionization chamber to allow ion packets to pass through at a fixed intervals corresponding to the measurement cycles.

A gate opening can be synchronized with the start of a data acquisition process of a measurement cycle to be the basis for measuring drift times of different ion species from the gate to the detector. In one embodiment, the ions can then be pulsed into a drift tube through the gate.

In a conventional stacked ring drift tube, the conductive rings can be formed from metal such as stainless steel, aluminum, brass or copper. Stainless steel is durable, but difficult to machine. Aluminum is lighter and softer to machine, but has a high thermal expansion coefficient that is unsuitable for operation at elevated temperatures. Brass and copper are suitably soft metals for machining, but brass may tarnish and copper can be highly chemically reactive and adsorptive to organic compounds. Insulating rings can be formed of a chemically inert, low cost, machinable material, such as glass, ceramic, mica and Teflon. Plastic and other materials that tend to off-gas may not be suitable. Polytetrafluoroethylene (PTFE) has good electrical properties and a high operating temperature, but a high thermal expansion coefficient.

However, according to one embodiment, the drift region may be defined by a single element drift tube (e.g., a monolithic resistive glass tube) to simplify the fabrication of the drift region as compared to the traditional stack ring configuration. Here, the application of an electric potential across the drift tube creates an electric gradient along its length. Ionized molecules travel through the drift tube toward the detector under the influence of a weak electric field.

As ionized molecules drift toward the detector under the influence of the electric field, they are slowed down by collisions with drift gas molecules being propelled in the opposite direction. Ion species with lower reduced mass, smaller collision area, and higher charge reach the detector faster. Ions are detected as they collide with, and are neutralized by, a detector. The collisions produce a small change in current, which may be amplified by a current amplifier. This signal can be synchronized to the gate pulse to yield a mobility spectrum, which is a plot of ion current versus ion drift time. The relative arrival times of the ionized molecules provide a characteristic spectrum used for presumptive identification of the substances present.

FIG. 1 is a block diagram illustrating an exemplary interconnection of elements of a detection instrument 100 using IMS in accordance with an embodiment of the present invention. The instrument 100 can include of a sample inlet 101 where vapors or particulate from the interrogated material (or sample) are collected. The instrument 100 can also include an ionization chamber 108 to receive the sample and a suction device 106 to draw the sample into the ionization chamber 108. A drift tube 111 receives the ionized sample from the ionization chamber 108. A high voltage supply 122 can be coupled to the ionization chamber 111 and the drift tube 111. The high voltage supply 122 can be used to create an electric field to propel the ionized sample away from the ionization chamber 108 through the drift tube 111. Further, an atmospheric pressure sensor 119, such as a barometer, can measure atmospheric pressure, such that the electric field can be adjusted based on atmospheric pressure. For example, the atmospheric pressure sensor 119 can measure atmospheric pressure inside the drift tube 111 or measure atmospheric pressure generally at the location of the instrument 100.

A drift gas supply 120 provides a drift gas that travels through the drift tube 111 towards the ionization chamber 108. Ionized molecules of the sample encounter an ion collector 112 (e.g., a detector) at an end of the drift tube 111, which generates a signal that can be amplified by an amplifier 124 couple to the ion collector 112. The amplified signal can be received by a computer 126 (e.g., any suitable processing device) for analysis. A magnitude of the electric field gradient can be adjusted such that types of molecules of a particular sample have a substantially similar drift time regardless of the atmospheric pressure at the time of the measurement.

Figure 2A:
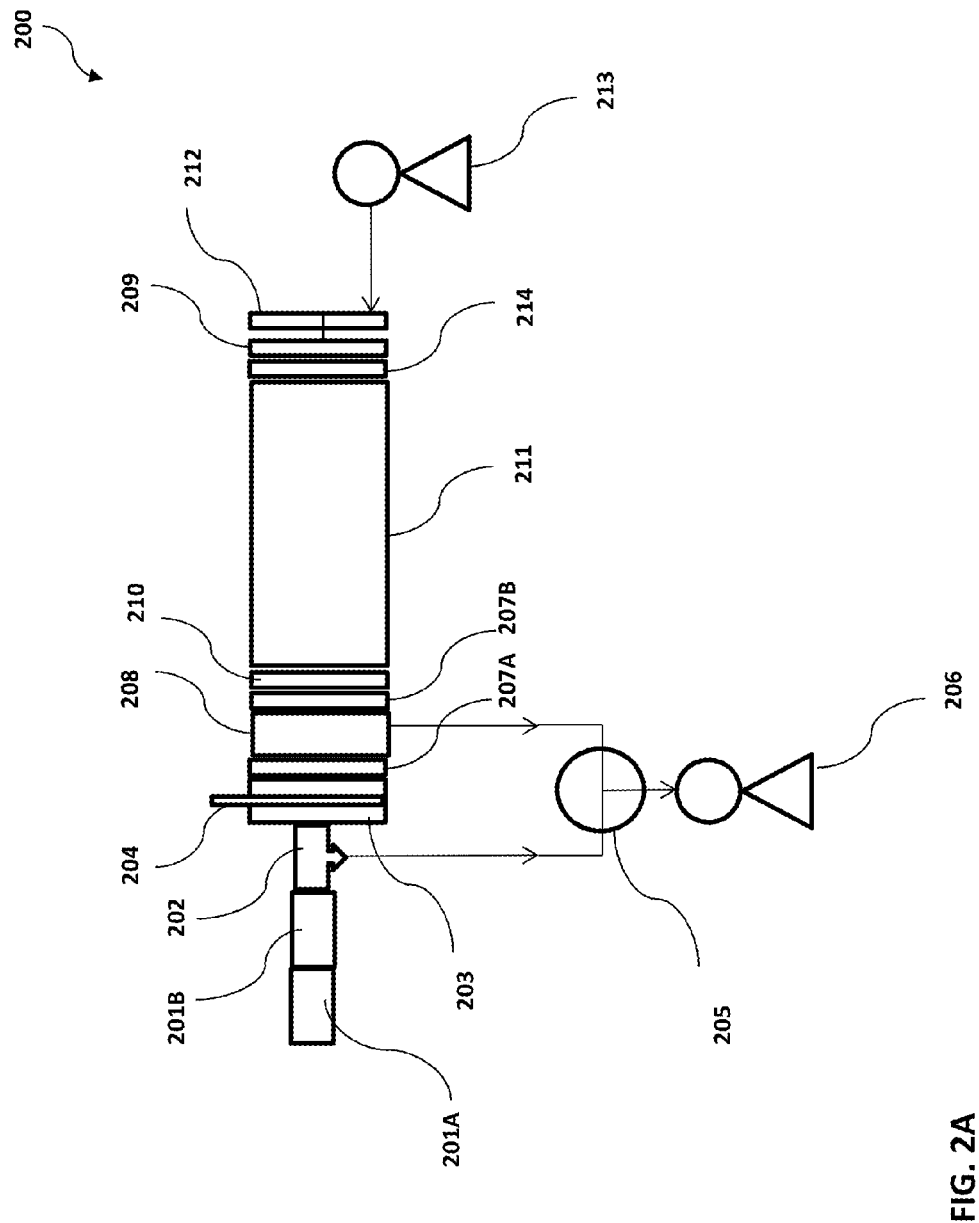
FIG. 2A is an illustrative view of a detection instrument using IMS in accordance with an embodiment of the present invention.
Figure 2B:
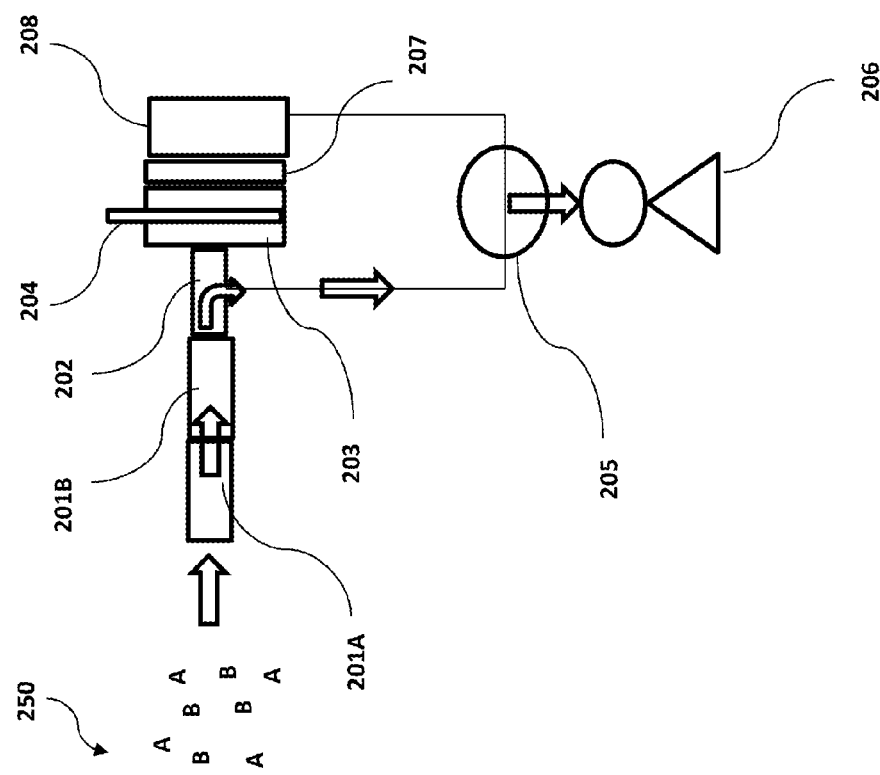
FIGS. 2B and 2C are illustrative views of a sample collection using the detection instrument of FIG. 2A, respectively, operable in a vapor mode and a particle mode in accordance with embodiments of the present invention.

FIG. 2A is an illustrative view of a detection instrument 200 using IMS in accordance with an embodiment of the present invention. In one embodiment, instrument 200 can be a portion of instrument 100 from FIG. 1. FIG. 2B illustrates sample collection when the instrument 200 of FIG. 2A is operating in vapor mode. When the instrument is used to analyze traces of vapor, a sample 250 may be first drawn through a desorber 201A and a vapor trap 201B by a pump 206 (e.g., a rotary vane or diaphragm pump) at a flow rate of about 1 L/min to about 10 L/min. The pump 206 can also be used draw the sample 250 through a coupler 202 (e.g., a T-connector fitting) that couples the pump 206, an ionization chamber 208, and the vapor trap 201B. In one embodiment, during the sample collection phase, a valve 205 (e.g., a mechanical 3-port valve solenoid) is set to couple the vapor trap 201B to the pump 206 to draw the sample 250 through the desorber 201A and into the vapor trap 201B. The desorber 201A can then thermally vaporize the sample 250. For example, during desorption, hot gas can be generated by applying an electrical current to a heating element (e.g., made of nichrome wire) positioned inside a tube (e.g., a glass or thermoplastic material tube) that is controlled by pulsed width modulation. Here, the temperature inside the desorber 201A can be ramped from ambient temperature to about 200 degrees C. in a short period of time, and desorption can take from about 1 second to about 10 second. The vapor trap 201B can include a trapping material such Tenax® coated silica, which maintains the sample 250 in the vapor trap 201B. The sample 250 may then be released into the ionization chamber 208 by switching the valve 205 to couple the ionization chamber 208 to the pump 206, and actuating the pump 206.

Figure 2C:
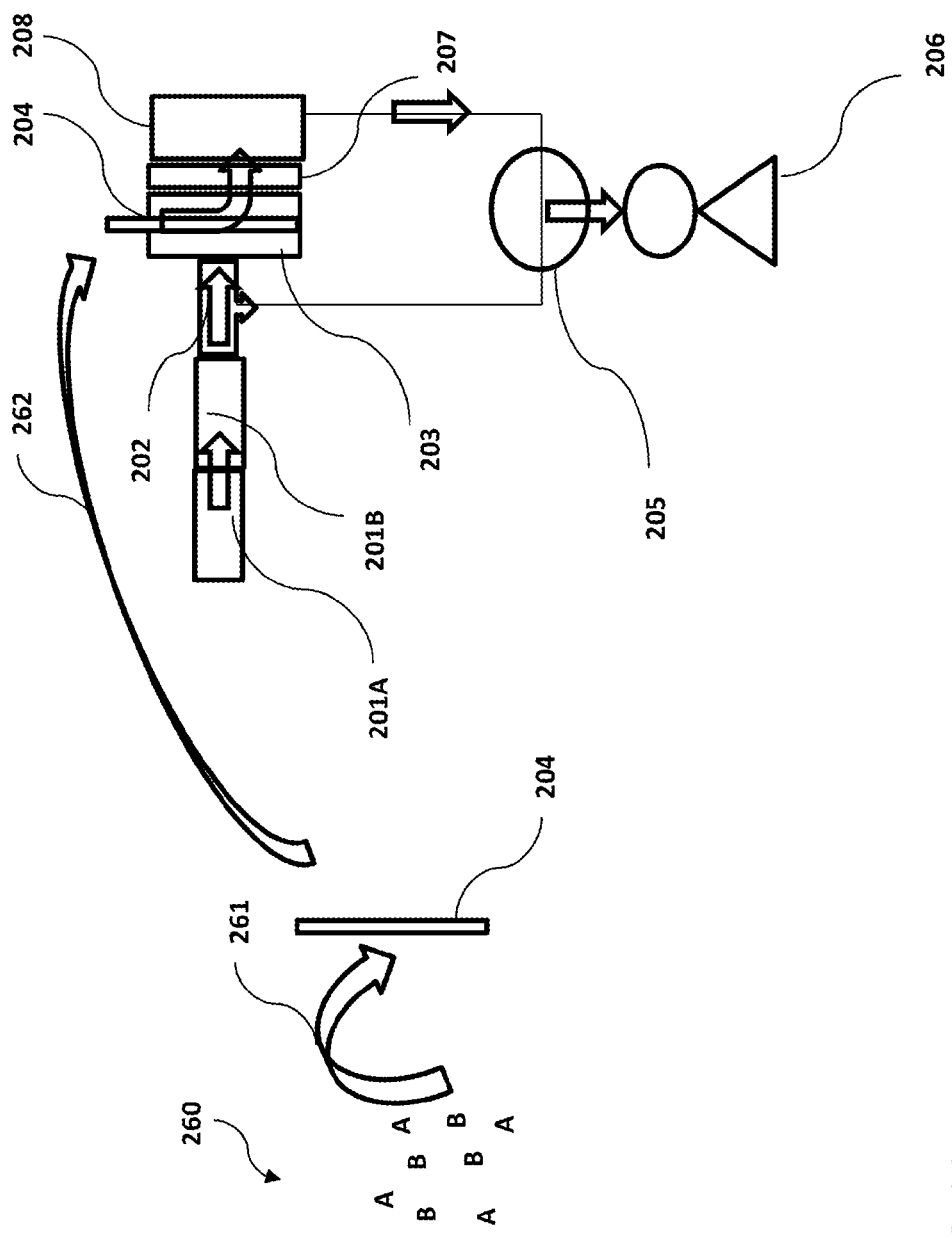

FIG. 2C illustrates a sample collection when the instrument 200 of FIG. 2A is operating in particle mode. When a particulate sample 260 is being analyzed, the particulate sample 260 can be collected onto a sampling screen 204 (e.g., made of thermal resistant material such as stainless steel mesh, Teflon, or glass fiber fabric), as shown by arrow 261. The sampling screen 204 may then be positioned, as shown by arrow 262, into a heated port 203 to thermally desorb the particulate from the sampling screen 204. The desorption process can take from about 1 second to about 10 seconds, and the heated port 203 can be maintained at a temperature in a range from about 100 degrees C. to about 200 degrees C. The desorbed sample can then be drawn into the ionization chamber 208 by setting the valve 205 to couple the pump 206 to the ionization chamber 208 and actuating the pump 206.

Figure 2D:
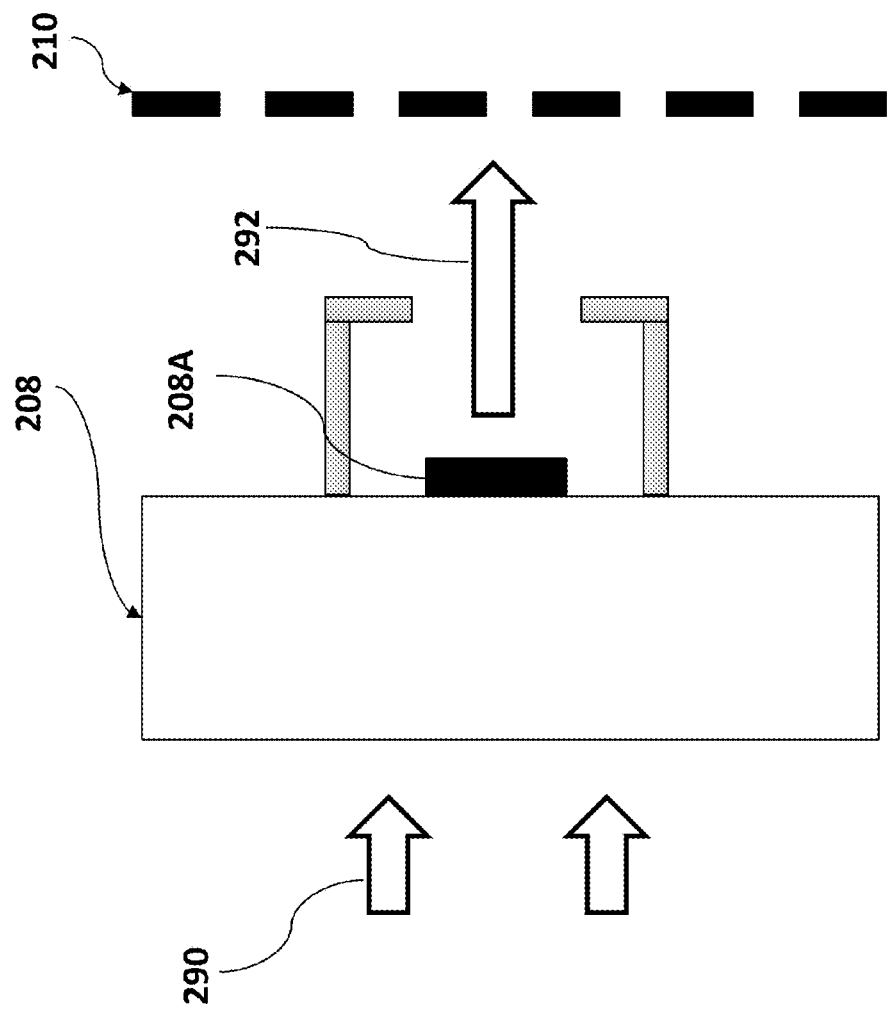
FIG. 2D is an illustrative view of ionization of a sample with a radioactive source in accordance with an embodiment of the present invention.

Returning to FIG. 2A, subsequent to either the vapor or particulate sample entering the ionization chamber 208, positive and negative ions are generated by exposing the sample to radioactive sources, such as $Ni^{63}$, or a corona discharge. In an embodiment shown in FIG. 2D, a sample is drawn into the ionization chamber 208, as shown by arrow 290. The sample is then exposed to a radioactive source 208A, which ionizes molecules of the sample. In another embodiment, a high voltage supply can be used to provide a corona discharge, which ionizes the molecules of the sample. The ionized molecules are kept inside the ionization chamber 208 by a gate 210 (e.g., consisting of a thin stainless steel mesh). The gate 210 can be opened for a period in a range from about 10 microseconds to about 400 microseconds to allow an ionized sample packet to move in a direction shown by arrow 292 to leave the ionization chamber 208. Short opening times can limit sensitivity, but if the gate opening time is too long, then peak broadening could result in poor resolution.

The ionization chamber 208 and the gate 210 are maintained at substantially the same electrical potential (e.g., in a range from about 1 KV to about 10 KV). Returning to FIG. A, to introduce the ionized sample packet into the drift tub 211, the ionization chamber 208 can be pulsed to a higher potential than the gate 210 by a voltage in a range from about 100 to about 1000V for a time in a range from about 10 to about 400 microseconds. This difference in potential pushes the ionized sample packet through the gate 210. The ionization chamber 208 may be electrically insulated from the heated port 203 and a gate 210 by two spacers 207A and 207B, which may be made of Teflon®, Peek® or other thermo plastic material.

Figure 2E:
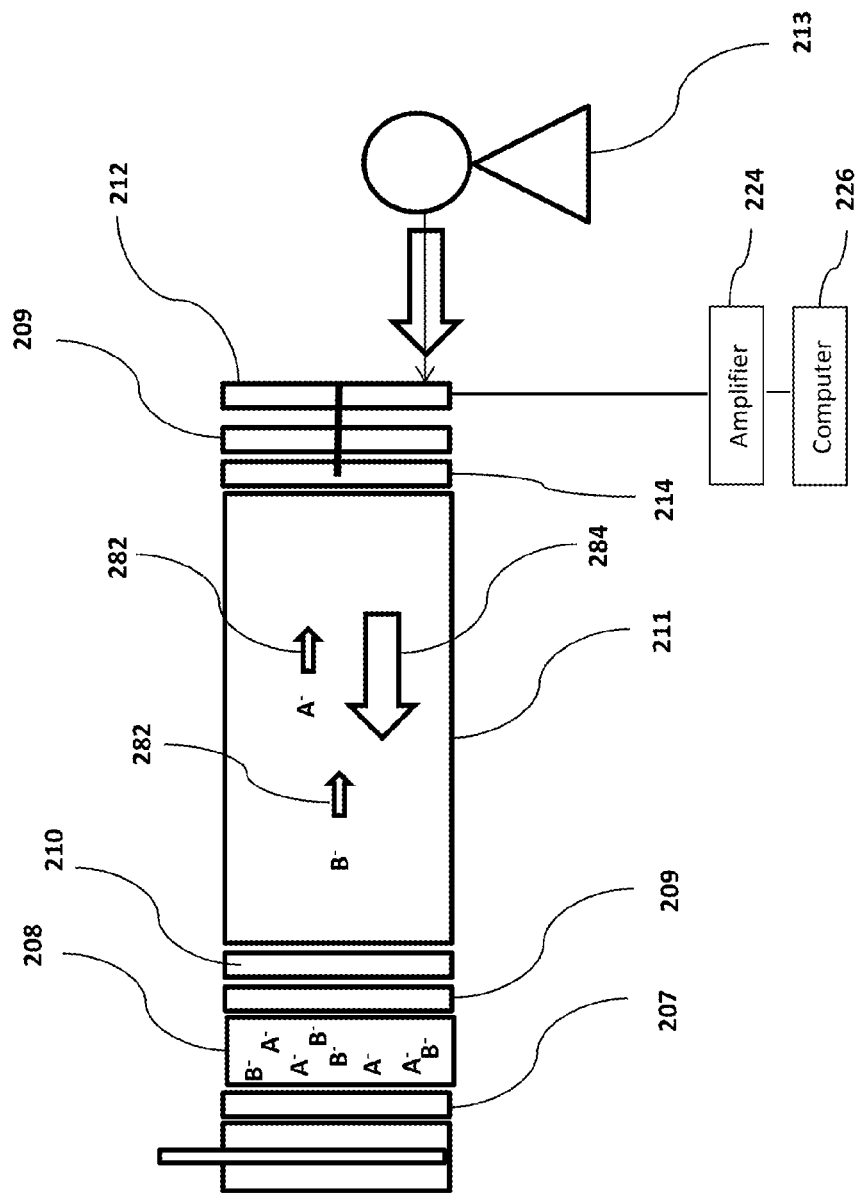
FIG. 2E is an illustrative view of ion drift in the detection instrument of FIG. 2A.

FIG. 2E is an illustrative view of ion drift in the instrument 200 of FIG. 2A. As shown in FIG. 2E, ionized molecules $A^-$ and $B^-$ of the sample drift through the drift tube 211 toward a detector 212 in a direction 282 under the influence of an electric field. The electric field, which can be generate by a high voltage supply, can be in a range from about $200\,V\cdot cm^{-1}$ to about $400\,V\cdot cm^{-1}$. In one embodiment, a resistive coating is located about the drift tube, and the electric field is applied to the resistive coating. The drift tube 211 can have a length in a range from about 5 cm to about 25 cm in length and a diameter (e.g., inner diameter) in a range from about 1 cm to about 5 cm. The drift tube can be formed of glass with a resistivity in a range from about 20 Mohms to about 200 Mohms. A drift gas can be propelled through the drift tube 211 by pump 213 (e.g., a rotary or diaphragm pump), as shown in FIG. 2A, towards ionization chamber 208. The ionized molecules $A^-$ and $B^-$ are slowed down by collisions with drift gas molecules traveling in an opposite direction 284. Ionized molecules are detected upon collision with, and neutralization by, a detector 212. The collisions produce a small change in current (an ion current), which can be amplified by an current amplifier 224.

In an embodiment, the detector is a Faraday plate, which is a circular metal disc that is placed at the end of the drift tube facing the incoming ionized molecules. The Faraday plate can be coupled to an inverting input of the current amplifier 224. When ionized molecules collide with the Faraday plate a current, e.g., a current in a range between about $10^{-10}$ amperes to about $10^{-11}$ amperes, is produced and amplified to a DC voltage in a range from about 1 V to about 10 V by the current amplifier 224. In an embodiment, a focusing ring 214 can focus the ionized molecules onto a detector. For example, the focusing ring 214 can focus the ionized molecules onto a pin type ion collector, which may result in a better signal to noise ratio. The focusing ring 214 can be insulated from the detector 212 by a spacer 209.

Figure 3:
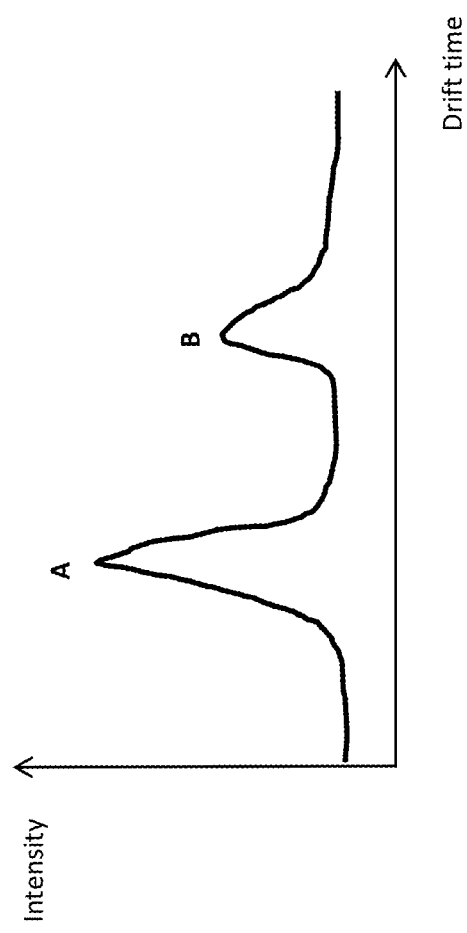
FIG. 3 is a charted diagram illustrating plasmagram generation based on ion drift in accordance with an embodiment of the present invention.

The amplified signal can then be received by a computer 226 for further analysis, where the signal can be synchronized to the opening of the gate 210. Ionized molecules with lower reduced mass, smaller collision area, and higher charge would likely reach the detector 212 faster. The ionized molecules relative arrival times provide a characteristic mobility spectrum (i.e., a plot of ion current versus ion drift time) used for presumptive identification of the substances present. The output DC voltage can be correlated to the ionized molecule signal intensity. Output from the detector can be an analog signal, which is then digitized and plotted on an x-y graph as the characteristic ion mobility spectrum. As illustrated in FIG. 3, the drift time of each ion species is plotted on the x-axis, starting at "0" (which corresponds to the gate opening), and the signal intensity (e.g., in arbitrary units or DC voltage) is plotted on the y-axis. Here, peak A indicates an arrival time of ionized molecules $A^-$ and peak B indicates an arrival time of ionized molecules $B^-$.

Figure 4:
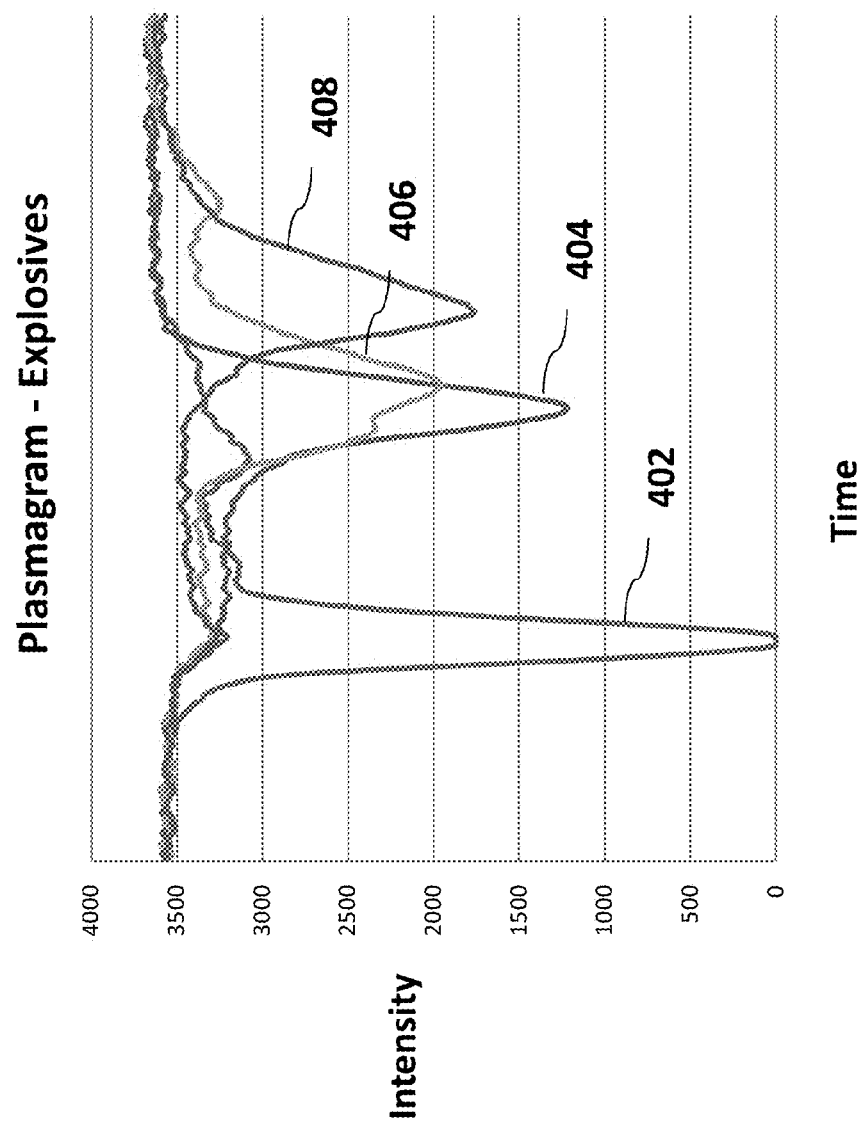
FIG. 4 is a charted diagram illustrating an explosives plasmagram in accordance with an embodiment of the present invention.
Figure 5:
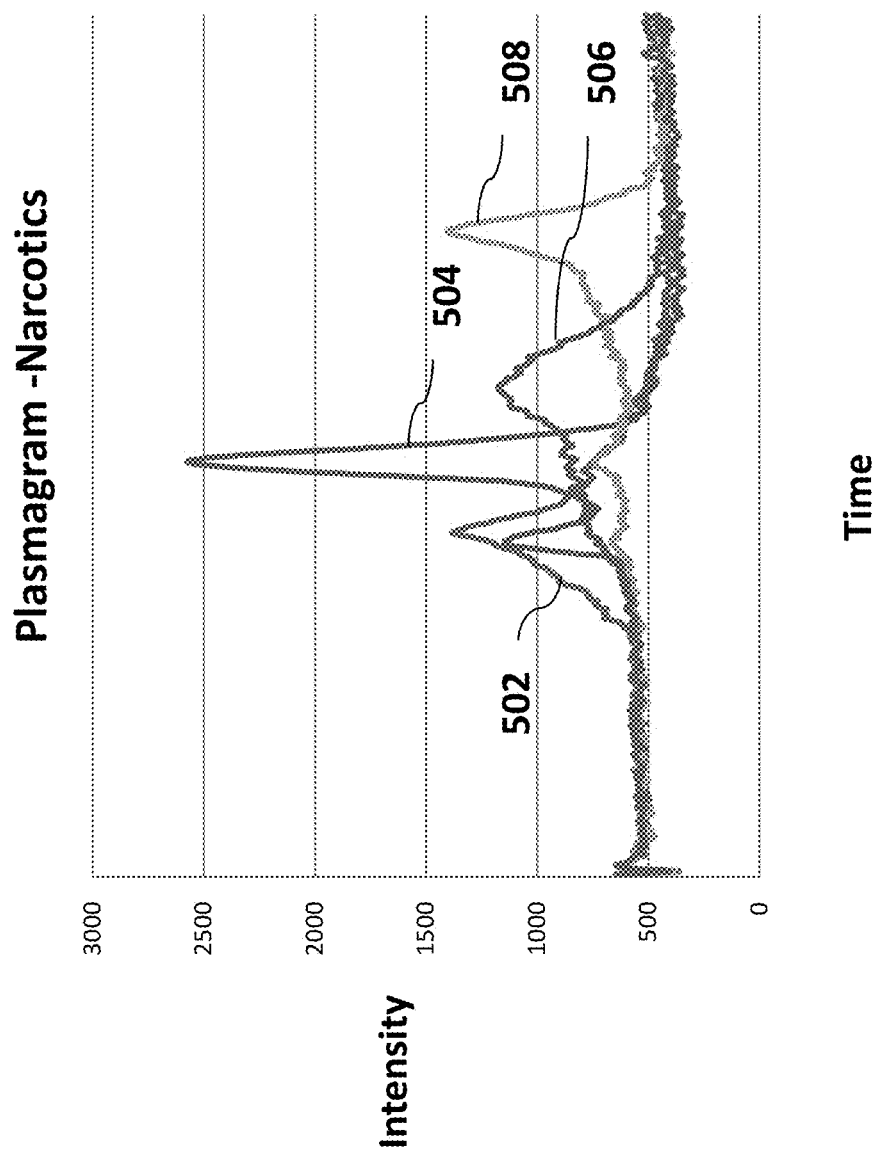
FIG. 5 is a charted diagram illustrating a narcotics plasmagram in accordance with an embodiment of the present invention.

According to an embodiment, the instrument described herein can be used in the field of security to detect the presence of illicit substances such as explosives, narcotics or chemical warfare agents. When operated to detect traces of explosives, the high voltage power supply can apply a negative voltage to the ionization chamber 208, the gate 210 and the drift tube 211. An IMS plasmagram, as illustrated in FIG. 4, can be obtained in the negative configuration for analyzing samples of explosive substances because electronegative functionality groups can be present in explosives, such as PETN 408, RDX 406, NG 404 or AN 402. Whereas plasmagrams can be obtained in the positive configuration for analyzing samples of narcotic substances because narcotic substances can generate stable positive ions, such as blank 502, cocaine 504, THC 506, and heroin 508, as illustrated in FIG. 5.

Figure 6:
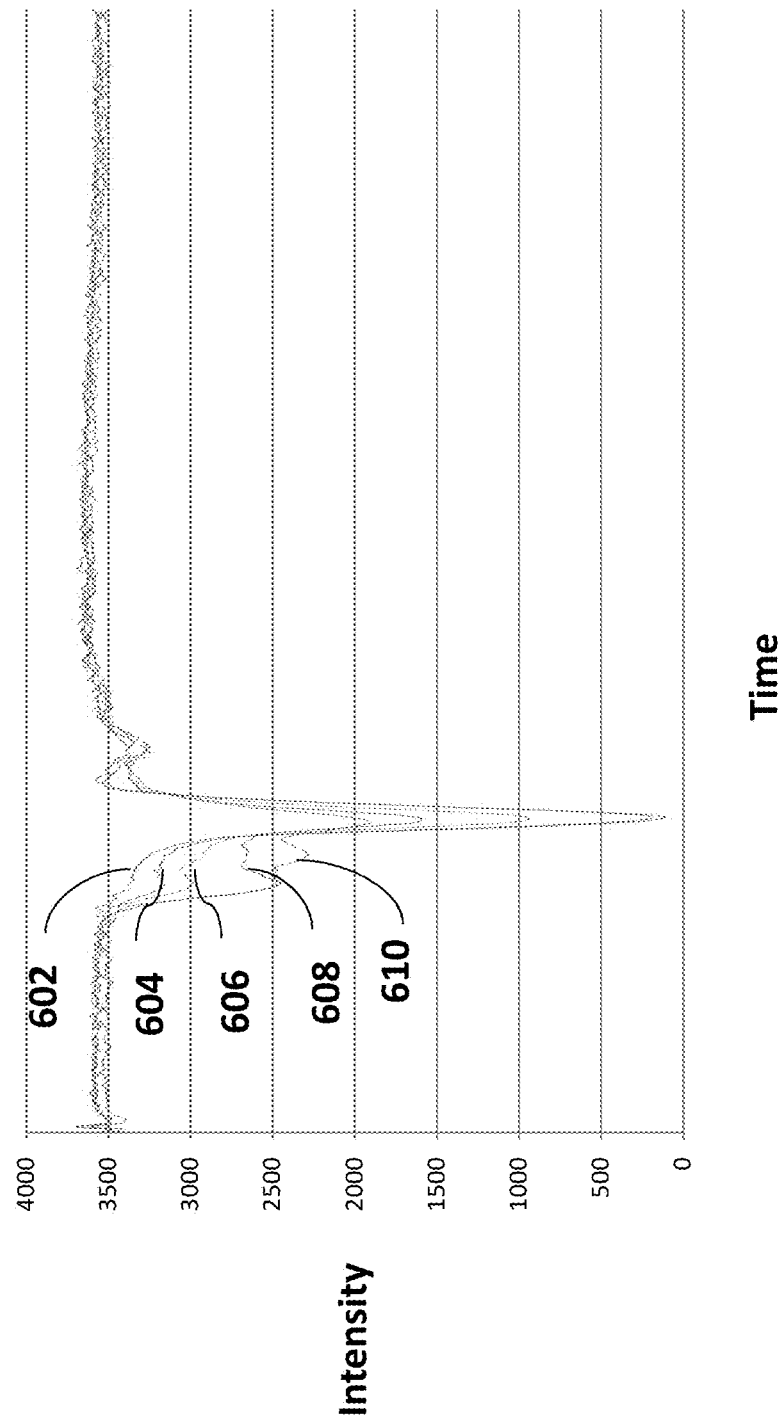
FIG. 6 is a charted diagram illustrating TNT plasmagrams in accordance with an embodiment of the present invention.
Figure 7:
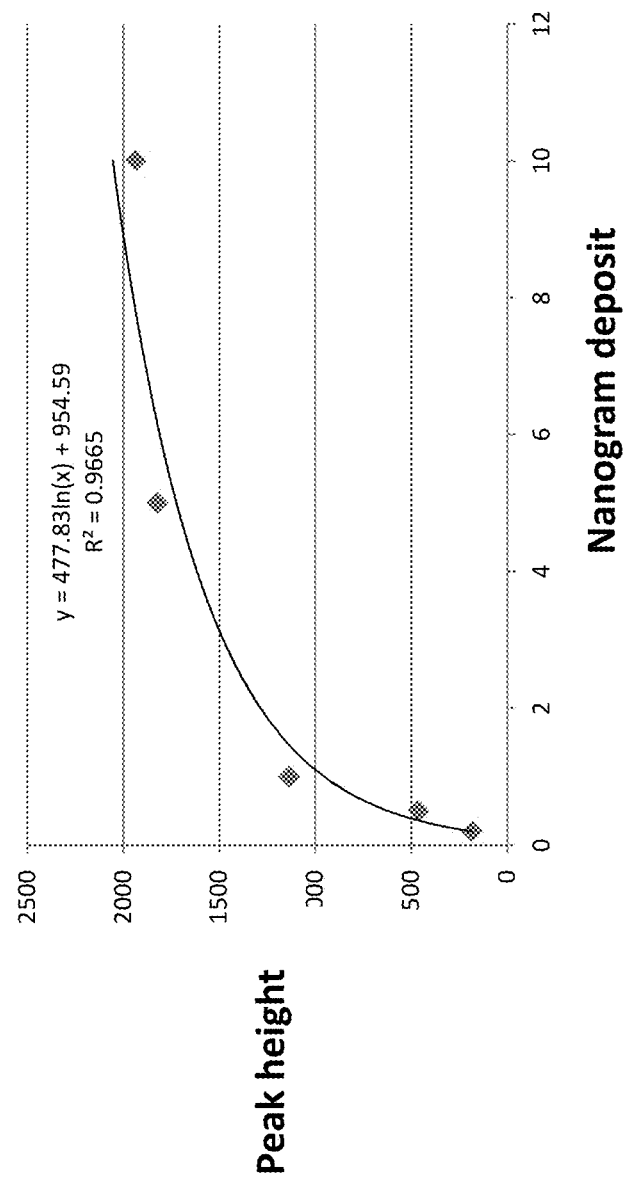
FIG. 7 is a charted diagram illustrating a TNT calibration curve in accordance with an embodiment of the present invention.

FIG. 6 is a charted diagram illustrating TNT plasmagrams in accordance with an embodiment of the present invention. FIG. 6 shows plasmagrams for TNT using 0.2 ng of TNT at sample 602, 0.5 ng of TNT at sample 604, 1.0 ng of TNT at sample 606, 5.0 ng of TNT at sample 608, and 10 ng of TNT at sample 610. FIG. 7 is a charted diagram illustrating a TNT calibration curve in accordance with an embodiment of the present invention. Here, the amount of TNT was varied from about 0.2 to about 10 ng to evaluate the linearity of the respond of different quantity of TNT. The results show that at quantities below about one nanogram, there is a linear response. However, the results also show that the response can saturate at quantities higher level than about 10 ng. The saturation may result from either the use of a low level radioactive source (e.g., about 100 microcurie to about 1000 microcurie) or a short resident time inside the ionization chamber. However, the plasmagrams of FIG. 7 show that a low level of $Ni^{63}$ generate measurements with sufficient dynamic range. This low level radioactivity is generally beneficial for practical use of an IMS instrument, because no special measures are required to handle and dispose this material.

In one embodiment, the geometry of the ionization chamber 208 can be optimized to allow the system to work with low level $Ni^{63}$ sources of 100 microcurie and yet retain a useful chemical dynamic range, as shown in FIG. 6 and FIG. 7. For example, the ionization chamber can be designed such that the sample flows onto the top of the radioactive source and is maintained in that location for a suitable period (e.g., by a gate) for the ionization process to occur.

According to one embodiment, characteristic average drift velocity $v_d$ ($cm \cdot s^{-1}$) of an ion species is governed by the electric field E ($V \cdot cm^{-1}$) and mobility coefficient (constant) K ($cm^2 \cdot V^{-1} \cdot s^{-1}$) through $v_d = K \cdot E$. When the instrument parameters and chemistries inside the drift tube are controlled, the mobility coefficient K ($cm^2 \cdot V^{-1} \cdot s^{-1}$) is governed by the size-to-charge ratio and the reduced mass of the ion in the supporting atmosphere. Thus, distinctions between different ion species are based on their mobility coefficient. The mobility coefficient can be expressed as the reduced mobility $K_0$ ($cm^2 \cdot V^{-1} \cdot s^{-1}$) in the equation below observed at standard pressure and temperature.

$$K_o = K \left[\frac{273}{T}\right]\left[\frac{P}{760}\right]$$

The length of time for an ion to drift to the collector is drift time ($t_d$) and is a function of the size and mass of the ion, the length of the drift tube ($l_d$), the strength of the electric field (E), the temperature (T) and Pressure (P), where:

$$v_d = l_d/t_d$$

Therefore the drift time for a given ion can be expressed:

$$t_d = (l_d/EK_0) \cdot (273/T) \cdot (P/760)$$

Environmental changes and other extraneous variables may cause changes in any of the measured peaks. Temperature T inside the instrument is a controllable parameter, but the atmospheric pressure is variable and can be much more difficult to control. Further, ambient atmospheric pressure changes can cause the peaks to shift in terms of drift time position.

Since the atmospheric pressure is a variable that is difficult to control, adjustment of a magnitude of the electric field E can be used to correct for this variation to obtain reproducible drift times ($t_d$) that are independent from variations of atmospheric pressure, according to one embodiment. For example, the atmospheric pressure can be monitored (e.g., by a barometer, such as an aneroid barometer, a cylindrical resonator barometer, or an electrostatic capacity barometer) so that when the atmospheric pressure increases, the magnitude of the electric field is increased by the same amount, such that the velocity of the ions remain the same. In one example, when atmospheric pressure increases by 5%, the velocity of the ions can remain the same by increasing the electric field by the same amount (i.e., 5%).

Figure 8A:
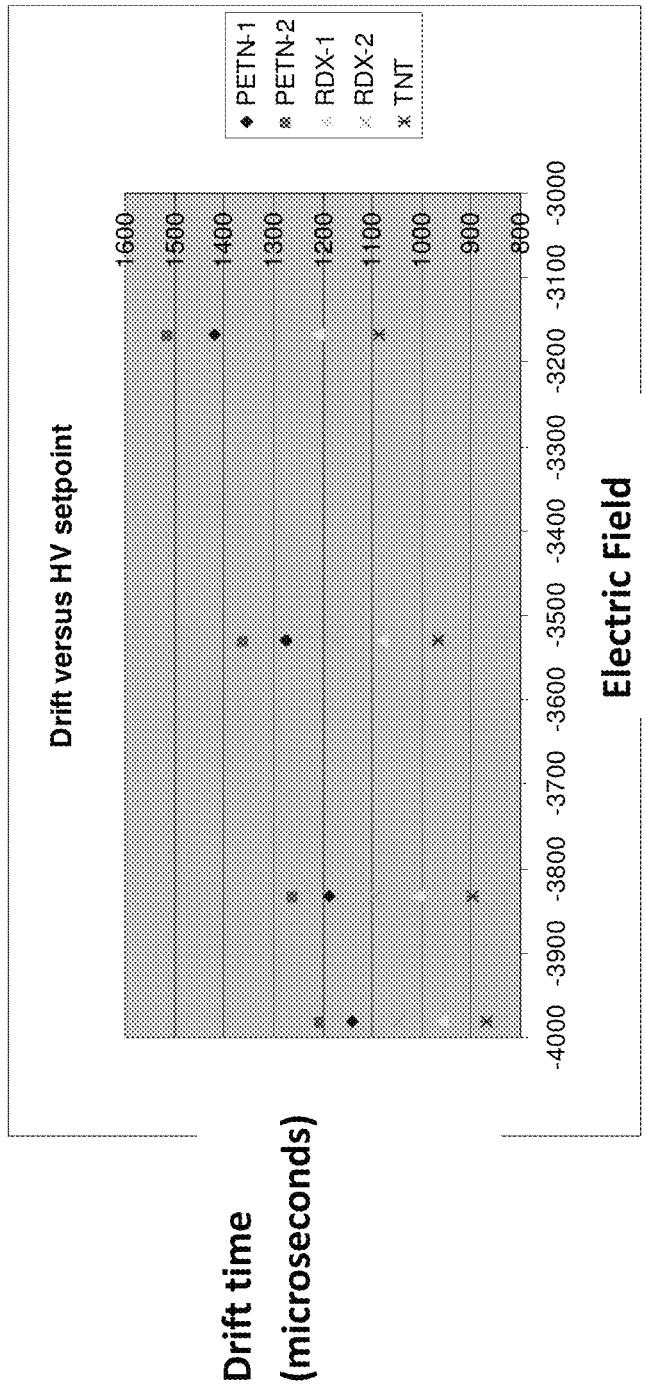
FIG. 8A is a charted diagram illustrating drift time versus electric field in accordance with an embodiment of the present invention.
Figure 8B:
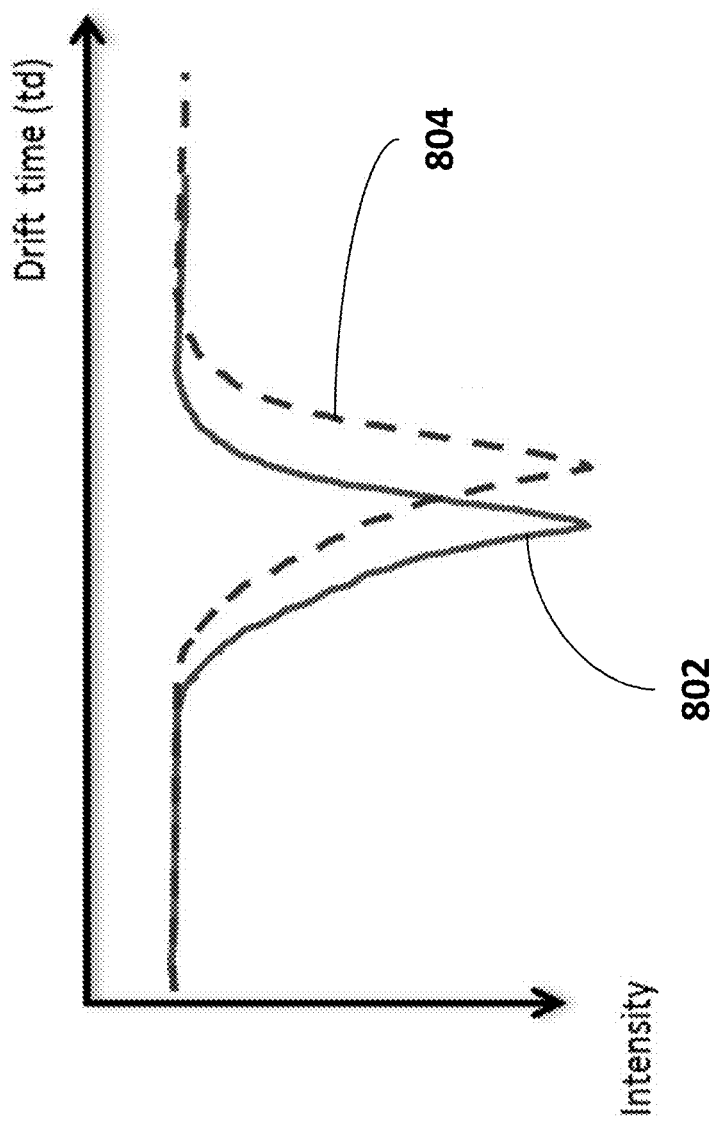
FIG. 8B is a charted diagram illustrating drift time versus intensity for an ion at two different atmospheric pressures with no electric field correction.
Figure 8C:
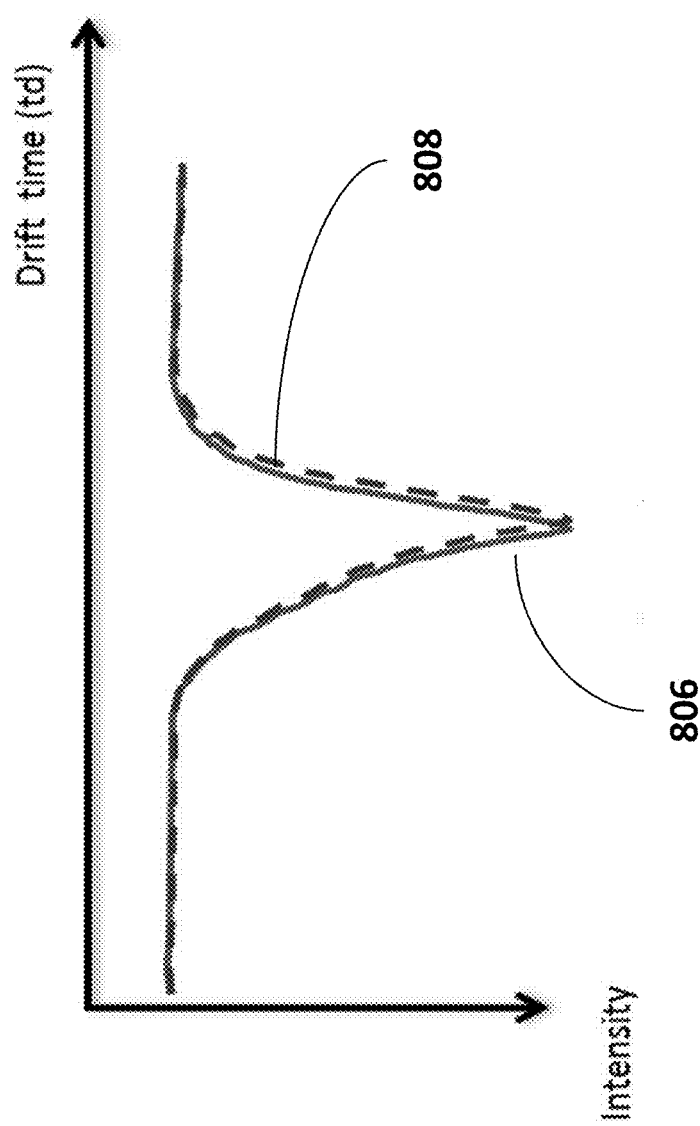
FIG. 8C is a charted diagram illustrating drift time versus intensity for an ion at two different atmospheric pressures with electric field correction.

The linear response of the drift time versus the electric field (i.e, applied high voltage) is illustrated in FIG. 8A, which shows that each chemical is responding similarly, in a linear fashion, to increases of electrical field inside the drift region. FIG. 8B illustrates drift time versus intensity for an ion at a certain atmospheric pressure 802 and for the same ion at a different atmospheric pressure 804, where there was no electric field correction for the variation in atmospheric pressure. Here, the arrival time of the peak intensity shifts as a result of the variation in atmospheric pressure. FIG. 8C illustrates drift time versus intensity for an ion at a certain atmospheric pressure 806 and for the same ion at a different atmospheric pressure 808, where electric field correction has been used to correct for variation in atmospheric pressure. Here, the arrival time of the peak intensity does not shift as result of the variation in atmospheric pressure because the electric field is varied in response to variations in atmospheric pressure.

In another embodiment, the drift tube is at ambient temperature, such that contamination present inside the drift tube can condense inside the drift tube (e.g., on an inner surface of the drift tube). Therefore, when the impurity remains inside the drift tube as condensation on an inner surface (rather than moving onto the detector), the impurity will not generate a signal.

Figure 9:
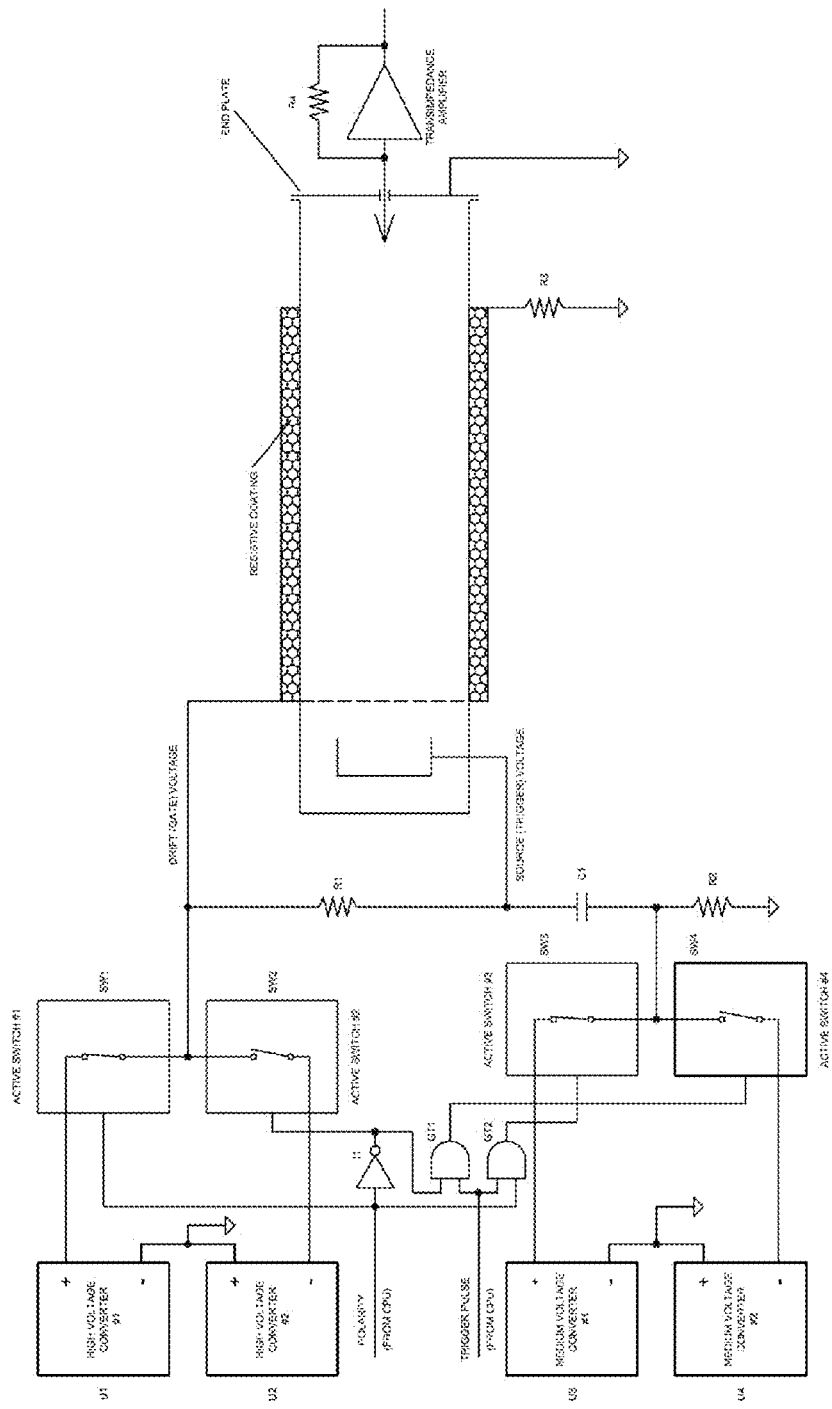
FIG. 9 is a high-voltage circuit diagram in accordance with an embodiment of the present invention.

FIG. 9 illustrates exemplary circuitry for a high voltage power supply which can be used to create the electrical field inside a drift tube of an instrument, according to an embodiment. In one embodiment, the instrument can be instrument 200 of FIG. 2A. The high voltage for the drift tube is supplied by two high voltage converters, U1 and U2, where U1 is for the positive mode (e.g., narcotics) and U2 is for the negative mode (e.g., explosives) respectively. Selection between the two polarities can be done by the active switches SW1 and SW3, which are driven in opposition by a POLARITY signal delivered from a CPU. Voltage for the high voltage supply can be inverted by the inverter I1. The action can be similar to a single pole, double throw (SPDT) relay, thus using two different HV converters for the two polarities allows the instrument to use different voltages for the two operating modes.

The high voltage from U1 to U2 high voltage power supply is applied to the gate and to an external resistive coating along the drift tube, which can achieve a constant voltage distribution along the tube and, therefore, a quasi-constant electric field in the tube. The resistive coating is coupled to the ground through resistor R3. Voltage drop across R3 creates an electric field in the terminal zone of the instrument, which helps concentrate the ionized molecules towards the detector (e.g., collecting pin). Ionized molecules which do not hit the collecting pin can transfer electrical charge to an end plate (e.g., Faraday plate), which is coupled to the ground. The ionized molecules which hit the collecting pin can create an input current to the amplifier, which can be converted to a voltage.

The source that propels the positive or negative ions through the drift tube can be polarized through R1 and can be maintained at the same voltage as the resistive coating of the drift tube. This voltage can be maintained for substantially the duration of a measurement cycle, except for the starting of the cycle, when a trigger pulse (trigger voltage) is applied. The pulse can be provided by two different medium voltage converters, U3 and U4, the first converter U3 for the positive (narcotics) mode and the second converter U4 for the negative (explosives) operating modes. Pulse polarity can be selected by the same logical signals as the high voltage applied to U1 and U2 and delivered for a short time at the beginning of the sampling cycle. This pulse application can be carried out by the two AND gates GT1 and GT2, which drive two active (MOSFET) switches SW3 and SW4.

During most of the cycle SW3 and SW4 are off and the boot-strap capacitor C1 is charged at the high voltage through the resistors R1 and R2. When SW3 and SW4 turns on, the pulse voltage will occur along R2, and C1 will "lift" the pulse voltage on top of the high voltage, causing the voltage on the source to be higher than the drift by the trigger pulse amplitude. This temporary electric field will "push" the ions in the drift zone of the drift tube.

In one embodiment, the apparatus can be optimized to be battery operated by reducing power consumption. Here, when the instrument is in idle mode, only the heated port 203 and the ionization chamber 208 are maintained at elevated temperatures of about 100 to 200° C. depending on the application. Both pumps 206 and 213 can be turned ON only while analyzing a sample. The desorber 200 can be pulse heated for a period of 1 to 10 seconds to vaporize the material that was previously trapped in the vapor trap 201. The high voltage power supply can also only be ON during the analysis phase. The drift tube can be operated at ambient temperature. As a result, the overall power consumption may be only 15 to 30 W.

Figure 10:
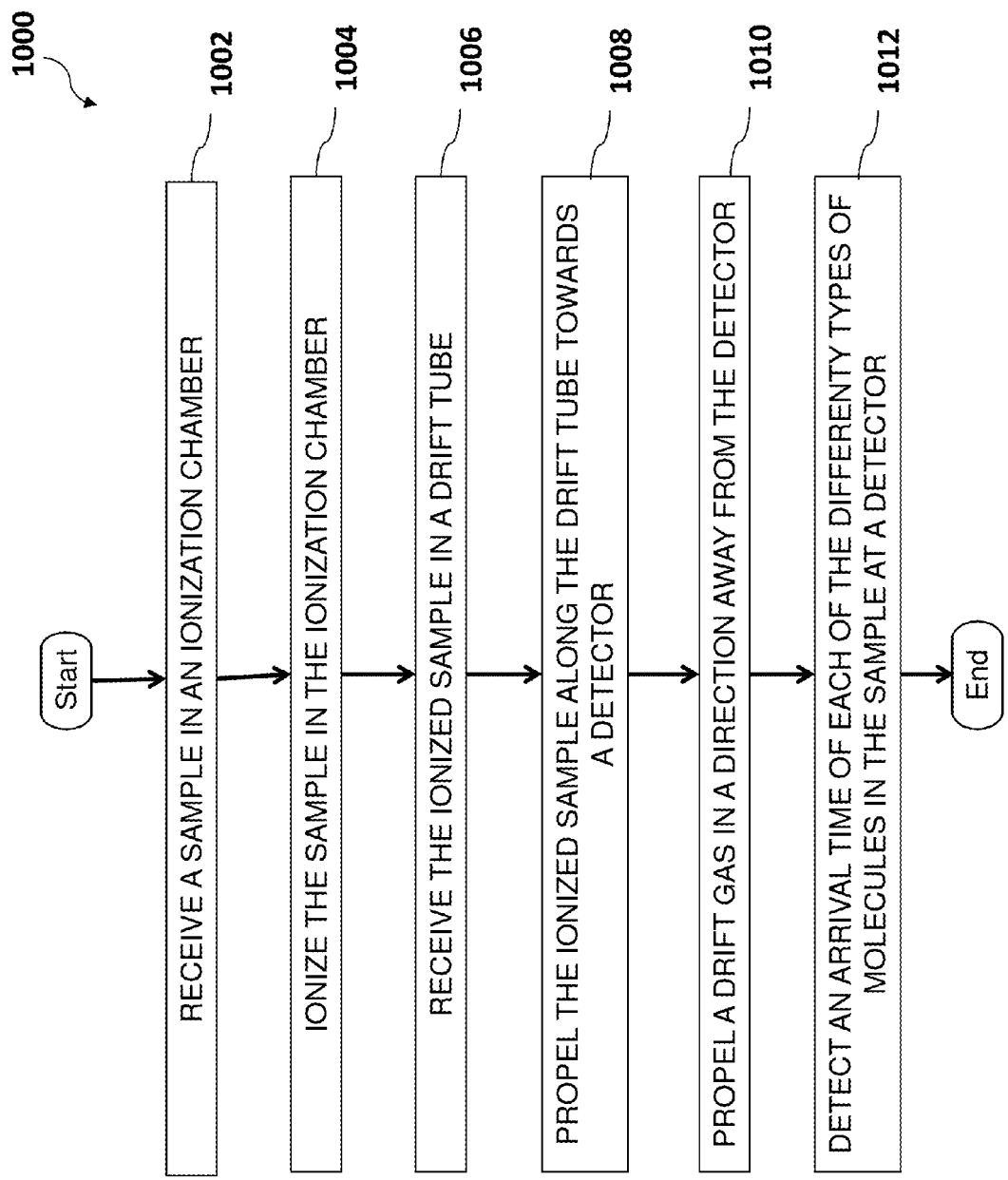
FIG. 10 illustrates a method of analyzing a substance according to one embodiment.

FIG. 10 illustrates a method 1000 of analyzing a substance according to one embodiment. The method 1000 can be performed with instrument 200 of FIG. 2A-D, according to one embodiment.

In block 1002, an ionization chamber receives a sample. For example, the sample can be a vapor sample that has been vaporized in a desorber, or a particulate sample that has been desorbed in a heated port. The sample can be drawn into the ionization chamber via a pump.

In block 1004, the sample is ionized in the ionization chamber. For example, the sample can be ionized by exposure to a radioactive substance or a corona discharge. As a result of the ionization, molecules of the sample acquire a charge by gaining or losing electrons.

In block 1006, the ionized sample is received in a drift tube. For example, the drift tube can be a monolithic drift tube (e.g., a glass tube) that is coupled at a first end to the ionization chamber. In one embodiment, the ionized sample is propelled through a gate between the ionization chamber and the drift tube by increasing a potential of the ionization chamber with respect to the gate.

In block 1008, the ionized sample is propelled away from the ionization chamber along a length of the drift tube coupled to the ionization chamber by an electric field gradient of the drift tube. For example, a voltage source can be coupled across the drift tube to create an electric field gradient along the drift tube. The magnitude of the electric field and the gradient can be adjusted to propel ionized molecules of the ionized sample through the drift tube. For example, the drift tube can have an electric field gradient that is more negative towards an end of the drift tube coupled to the ionization chamber. If the ionized molecules exiting the ionization chamber have a negative charge, the ionized molecules will drift, or be propelled, away from the more negative end of the drift tube. Further, the magnitude of the electric field can be adjusted in view of an atmospheric pressure measurement (e.g., via a barometer) to calibrate a drift time of the ionized sample through the drift tube.

In block 1010, a drift gas is propelled from a drift gas supply through the drift tube in a direction opposite the direction of movement of the ionized molecules. Ionized molecules with lower reduced mass, smaller collision area, and higher charge travel faster through the drift tube because these molecules will be slowed less by the drift gas. As a result, different types of molecules of the ionized sample travel through the drift tube at different rates.

In block 1012, an arrival time of each of the different types of molecules is detected at a detector located at an end of the drift tube opposite the ionization chamber. The detector can be coupled an amplifier and a computer such that a signal based on the arrival times of the different types of molecules can be further analyzed. The ionized molecules relative arrival times can provide a characteristic mobility spectrum used for presumptive identification of the substances present.

Whereas many alterations and modifications of the present invention will no doubt become apparent to a person of ordinary skill in the art after having read the foregoing description, it is to be understood that any particular embodiment shown and described by way of illustration is in no way intended to be considered limiting. Therefore, references to details of various embodiments are not intended to limit the scope of claims, which in themselves recite only those features regarded as the invention.

The invention claimed is:

1. An apparatus for analyzing a sample, the apparatus comprising:
    an ionization chamber that receives and ionizes molecules of the sample;
    a drift tube coupled to the ionization chamber at a first end of the drift tube that receives the sample from the ionization chamber, the drift tube having an electric field gradient along a length of the drift tube that propels the sample in a first direction away from the ionization chamber, wherein a magnitude of the electric field gradient is in view of an atmospheric pressure measurement;
    a drift gas supply coupled to the drift tube that propels a drift gas through the drift tube in a second direction opposite the first direction such that different types of the ionized molecules of the sample travel through the drift tube at different rates; and
    a detector at a second end of the drift tube opposite the first end that detects an arrival time of each of the different types of the ionized molecules.

2. The apparatus of claim 1 further comprising a suction device coupled to the ionization chamber that draws the sample into the ionization chamber.

3. The apparatus of claim 1 further comprising a gate between the ionization chamber and the drift tube to maintain the sample in the ionization chamber until the gate is opened when a measurement cycle is initiated.

4. The apparatus of claim 3, wherein the ionization chamber and the gate have a substantially similar electrical potential until a measurement cycle is initiated and an electrical potential of the ionization chamber is pulsed to propel the ionized sample into the drift tube.

5. The apparatus of claim 1, wherein the drift tube comprises glass.

6. The apparatus of claim 1, wherein the detector is a Faraday plate collector.

7. The apparatus of claim 1 further comprising a focusing ring located between the drift tube and the detector that directs the ionized molecules towards the detector.

8. The apparatus of claim 7, wherein the detector comprises a pin collector, and wherein the focusing ring directs the ionized molecules towards the pin collector.

9. The apparatus of claim 1 further comprising a heated port coupled to the ionization chamber, where the heated port receives sample particulate on a sampling screen and desorbs the sample particulate from the sampling screen into the ionization chamber.

10. A method of analyzing a sample, the method comprising:
    receiving the sample by an ionization chamber;
    ionizing molecules of the sample by the ionization chamber;
    receiving the sample from the ionization chamber by a drift tube coupled at a first end to the ionization chamber;
    propelling the sample along a length of the drift tube in a first direction away from the ionization chamber by an electric field gradient of the drift tube, wherein a magnitude of the electric field gradient is in view of an atmospheric pressure measurement;
    propelling a drift gas from a drift gas supply coupled to the drift tube through the drift tube in a second direction opposite the first direction such that different types of the ionized molecules of the sample travel through the drift tube at different rates; and
    detecting an arrival time of each of the different types of the ionized molecules at a detector located at a second end of the drift tube opposite the first end.

11. The method of claim 10 further comprising drawing the sample into the ionization chamber via a suction device.

12. The method of claim 10 further comprising maintaining the sample in the ionization chamber via a gate until the gate is opened when a measurement cycle is initiated.

13. The method of claim 12 further comprising:
    maintaining the ionization chamber and the gate at a substantially similar electrical potential; and
    upon initiation of a measurement cycle, pulsing the electrical potential of the ionization chamber to propel the sample into the drift tube.

14. The method of claim 10, wherein the drift tube comprises glass.

15. The method of claim 10, wherein the detector is a Faraday plate collector.

16. The method of claim 10 further comprising directing the ionized molecules towards the detector via a focusing ring.

17. The method of claim 16, wherein the detector comprises a pin collector, and wherein the focusing ring directs ionized molecules towards the pin collector.

18. The method of claim 10 further comprising:
    receiving sample particulate on a sampling screen by a heated port; and
    desorbing the sample particulate from the sampling screen into the ionization chamber.

19. The method of claim 10, wherein ionizing the molecules of the sample comprises exposing the molecules of the sample to a radioactive source having radioactivity in a range from about 100 microcurie to about 1000 microcurie.

* * * * *